United States Patent
Wrbanek et al.

(10) Patent No.: US 8,159,669 B2
(45) Date of Patent: *Apr. 17, 2012

(54) SPACE RADIATION DETECTOR WITH SPHERICAL GEOMETRY

(75) Inventors: John D. Wrbanek, Sheffield Village, OH (US); Gustave C. Fralick, Middleburg Heights, OH (US); Susan Y. Wrbanek, Sheffield Village, OH (US)

(73) Assignee: The United States of America as represented by the Administrator of National Aeronautics and Space Administration, Washington, DC (US)

( * ) Notice: Subject to any disclaimer, the term of this patent is extended or adjusted under 35 U.S.C. 154(b) by 43 days.

This patent is subject to a terminal disclaimer.

(21) Appl. No.: 12/972,624

(22) Filed: Dec. 20, 2010

(65) Prior Publication Data

US 2011/0127437 A1    Jun. 2, 2011

Related U.S. Application Data

(62) Division of application No. 12/285,173, filed on Sep. 30, 2008, now Pat. No. 7,872,750.

(51) Int. Cl.
*G01N 15/02* (2006.01)

(52) U.S. Cl. ........................................ 356/336; 356/338
(58) Field of Classification Search .......... 356/335–343, 356/218–222; 250/305–308, 336.1, 363.01–363.05, 250/370.01, 370.14, 368–369, 207; 313/532–533, 313/381–382; 252/301 R
See application file for complete search history.

(56) References Cited

U.S. PATENT DOCUMENTS

| | | | | |
|---|---|---|---|---|
| 3,805,075 | A * | 4/1974 | Roberts | 250/366 |
| 4,564,753 | A * | 1/1986 | van Aller et al. | 250/214 VT |
| 5,665,971 | A * | 9/1997 | Chen et al. | 250/385.1 |
| 2008/0191134 | A1 * | 8/2008 | Almogy et al. | 250/307 |

* cited by examiner

*Primary Examiner* — Tri T Ton
(74) *Attorney, Agent, or Firm* — Robert H. Earp, III

(57) ABSTRACT

A particle detector is provided, the particle detector including a spherical Cherenkov detector, and at least one pair of detector stacks. In an embodiment of the invention, the Cherenkov detector includes a sphere of ultraviolet transparent material, coated by an ultraviolet reflecting material that has at least one open port. The Cherenkov detector further includes at least one photodetector configured to detect ultraviolet light emitted from a particle within the sphere. In an embodiment of the invention, each detector stack includes one or more detectors configured to detect a particle traversing the sphere.

20 Claims, 4 Drawing Sheets

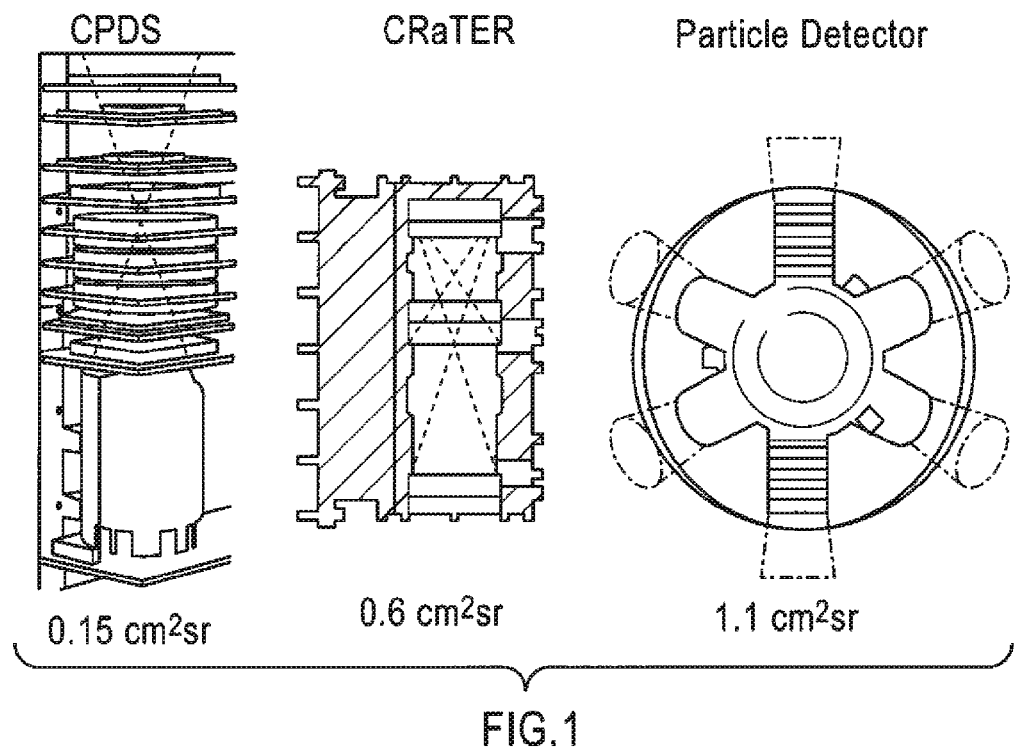
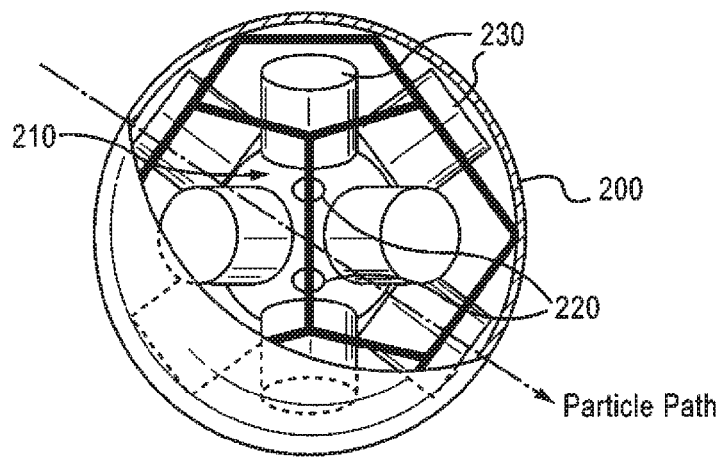
FIG.1
FIG.2

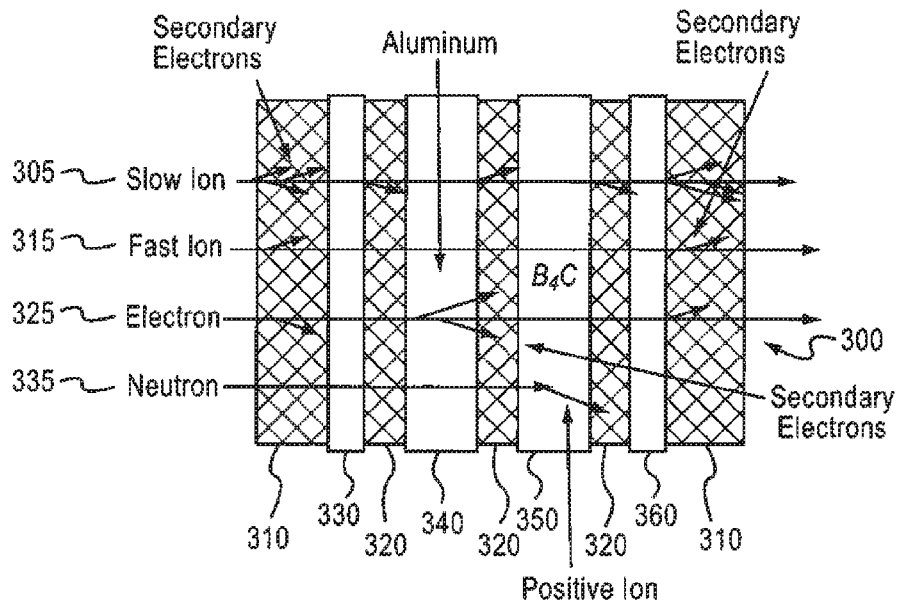

FIG.3

Cherenkov light emission energy per unit of path length:

$$\left(\frac{dE}{dx}\right) = \frac{(ze)^2}{c^2} \int_{n(\omega)>1/\beta} \omega\left(1-\frac{1}{\beta^2 n(\omega)^2}\right)d\omega$$

Light from $z$ ion: $\sim z^2 \cdot 2r$
Light from $z+1$ ion: $\sim (z+1)^2 \cdot L$

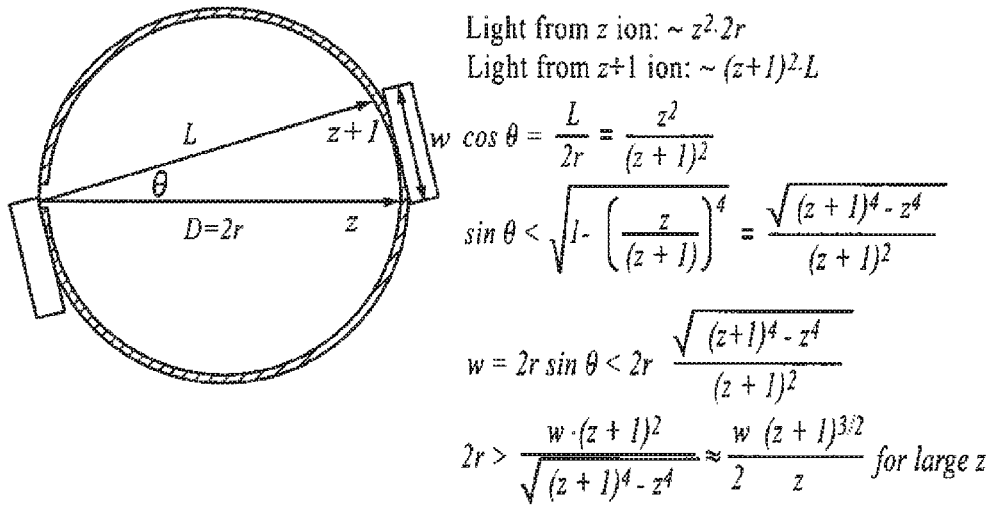

$$w \cos\theta = \frac{L}{2r} = \frac{z^2}{(z+1)^2}$$

$$\sin\theta < \sqrt{1-\left(\frac{z}{(z+1)}\right)^4} = \frac{\sqrt{(z+1)^4 - z^4}}{(z+1)^2}$$

$$w = 2r\sin\theta < 2r\frac{\sqrt{(z+1)^4 - z^4}}{(z+1)^2}$$

$$2r > \frac{w \cdot (z+1)^2}{\sqrt{(z+1)^4 - z^4}} \approx \frac{w \cdot (z+1)^{3/2}}{2} \cdot \frac{1}{z} \text{ for large } z$$

FIG.4

SPACE RADIATION DETECTOR WITH SPHERICAL GEOMETRY

CROSS-REFERENCE TO RELATED APPLICATIONS

This application is a divisional of U.S. patent application Ser. No. 12/285,173, entitled SPACE RADIATION DETECTOR WITH SPHERICAL GEOMETRY by the same inventors and having a filing date of Sep. 30, 2008 now U.S. Pat. No. 7,872,750.

STATEMENT REGARDING FEDERALLY SPONSORED RESEARCH OR DEVELOPMENT

The invention described herein was made by an employee (or employees, as appropriate) of the United States Government and may be manufactured and used by or for the Government for Government purposes without the payment of any royalties thereon or therefore.

BACKGROUND OF THE INVENTION

1. Field of the Invention

The present invention relates generally to particle detectors, and particularly radiation particle detectors.

2. Description of the Related Art

A need has been identified for new instrumentation and sensing capabilities to collect and process scientific data. For instance, NASA's Science Mission Directorate (SMD) has outlined specific needs for compact space radiation particle detectors, such as improved energy range and resolution, angle coverage and resolution, and particle species/charge identification. Space radiation is a constant and significant hazard to a crew engaged in space missions, and their equipment. The timely and accurate detection of space radiation particles is vital to the viability of these missions.

SUMMARY OF THE INVENTION

Some embodiments of the invention can provide an apparatus, which includes a spherical detector. The spherical detector includes a sphere of ultraviolet transparent material, where the sphere is coated by an ultraviolet reflecting material, that includes an open port, and a photodetector configured to face the open port. The apparatus further includes a pair of detector stacks mounted to the spherical detector, each detector stack including a detector configured to detect a particle so that the pair of detector stacks determines a path length and a path direction of the particle. The photodetector is configured to detect ultraviolet light emitted from the particle, so that the photodetector determines a charge, an energy, and a velocity of the particle.

Furthermore, some embodiments of the invention can provide an apparatus, which includes a spherical detector. The spherical detector includes a sphere of ultraviolet transparent material, where the sphere is coated by an ultraviolet reflecting material, that includes an open port, and a photodetector configured to face the open port. The apparatus further includes a pair of scintillation counters mounted to the spherical detector, each scintillation counter including a detector configured to detect a particle so that the pair of scintillation counters determines a path length and a path direction of the particle. The photodetector is configured to detect ultraviolet light emitted from the particle, so that the photodetector determines a charge, an energy, and a velocity of the particle.

Furthermore, some embodiments of the invention can provide a method for detecting radiation. The method includes providing a spherical detector including a sphere of ultraviolet transparent material, where the sphere is coated by an ultraviolet reflecting material, that includes an open port, and a photodetector configured to face the open port. The method further includes providing a pair of detector stacks mounted to the spherical detector, each detector stack including a detector. The method further includes detecting a particle, at each detector of the pair of detector stacks, so that the pair of detector stacks determines a path length and a path direction of the particle. The method further includes detecting ultraviolet light emitted from the particle, so that the photodetector determines a charge, an energy, and a velocity of the particle.

Furthermore, some embodiments of the invention can provide a method for detecting radiation, the method includes providing a spherical detector including a sphere of ultraviolet transparent material, where the sphere is coated by an ultraviolet reflecting material, that includes an open port, and a photodetector configured to face the open port. The method further includes providing a pair of scintillation counters mounted to the spherical detector, each detector stack including a detector. The method further includes detecting a particle, at each detector of the pair of scintillation counters, so that the pair of scintillation counters determines a path length and a path direction of the particle. The method further includes detecting ultraviolet light emitted from the particle, so that the photodetector determines a charge, an energy, and a velocity of the particle.

Furthermore, some embodiments of the invention can provide an apparatus. The apparatus includes first detecting means for detecting a particle and for determining a path length and a path direction of the particle. The apparatus further includes second detecting means for detecting ultraviolet light emitted from the particle, so that the second detecting means determines a charge, an energy, and a velocity of the particle.

BRIEF DESCRIPTION OF THE DRAWINGS

For proper understanding of the invention, reference should be made to the accompanying drawings, wherein:

FIG. 1 illustrates an example embodiment of a particle detector according to and embodiment of the present invention.

FIG. 2 illustrates another example embodiment of a particle detector, according to an embodiment of the present invention.

FIG. 3 illustrates an example embodiment of a detector stack of the particle detector, according to an embodiment of the present invention.

FIG. 4 illustrates a geometry to define a minimum Cherenkov sphere diameter of the particle detector, according to another embodiment of the present invention.

DETAILED DESCRIPTION OF THE PREFERRED EMBODIMENT(S)

Figure 5:
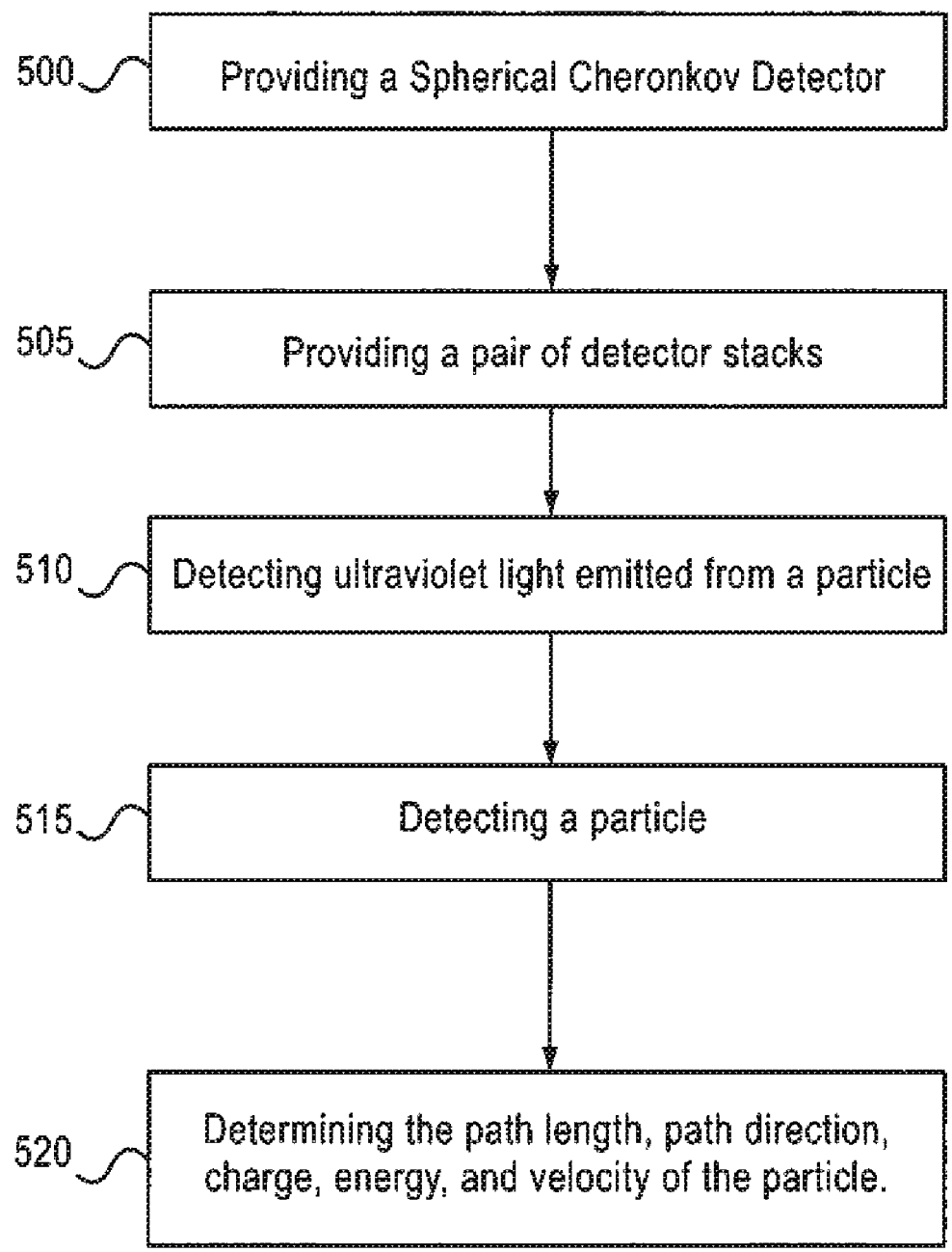
FIG. 5 illustrates a method of detecting a particle, according to another embodiment of the present invention.

It will be readily understood that the components of the present invention, as generally described and illustrated in the figures herein, may be arranged and designed in a wide variety of different configurations. Thus, the following detailed description of the embodiments of an apparatus, and method for detecting a particle, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of "certain embodiments," "some embodiments," or other similar language, throughout this specification refers to the fact that a particular feature, structure, or characteristic described in connection with the embodiment may be included in at least one embodiment of the present invention. Thus, appearances of the phrases "in certain embodiments," "in some embodiments," "in other embodiments," or other similar language, throughout this specification do not necessarily all refer to the same group of embodiments, and the described features, structures, or characteristics may be combined in any suitable manner in one or more embodiments.

A Cherenkov detector is a particle detector utilizing the velocity-dependent threshold energy of Cherenkov radiation. Cherenkov radiation is electromagnetic radiation emitted when a charged particle passes through a dielectric medium at a speed greater than the speed of light in that medium. Specifically, where the velocity of a charged particle is greater than the phase velocity of electromagnetic fields in a medium with an index of refraction greater than 1, the charged particle may emit energy per unit of a path length due to its electric field reacting to the dielectric polarization of the medium. The effect was first reported by P. A. Cherenkov in 1934, and bears his name. A Cherenkov detector allows for the discrimination between a lesser charged particle (which radiates less) and a more highly charged particle (which radiates more).

The SMD has identified that a key aspect of direct particle and field measurement is the miniaturization and reduction in mass and power needs required to enable multi-spacecraft missions, and missions that, because of the significant propulsion requirements levied by their extreme deployments, are very limited in their support to payload mass and power.

The Science Instruments and Sensor Capabilities Road Map (SIS CRM) and the design goals of existing cosmic ray detectors define technology requirements. These requirements include compact sensors with better energy/angle coverage, and highly integrated signal processing. New, robust compact detectors are needed to allow future detector packages with more options in satisfying specific mission goals. The current technology obstacles preventing the satisfaction of the specific mission goals include detector size, noise floor, and detection geometry.

For measurement of space radiation particles, previous detectors do not have the required miniaturized and integrated structure to fulfill the needs for compact space radiation particle detectors, outlined in the SIS CRM. Some detectors include the Charged Particle Directional Spectrometers (CPDS) on the International Space Station (ISS) and the Cosmic Ray Telescope for the Effects of Radiation (CRaTER) on the Lunar Reconnaissance Orbiter (LRO).

The ISS is a complex made of a series of modules provided by a consortium of nations. The ISS includes the CPDS instruments to provide radiation monitoring data for use in operational monitoring, such as indicating the radiation level during a solar particle event. The CPDS instruments include three coincidence triggers using, for instance, 1 mm thick compensated silicon detectors, three position-sensitive detectors, and six 5 mm thick compensated silicon detectors. A Cherenkov detector includes a 5 cm diameter by 1 cm thick sapphire disk on a photomultiplier tube. Due to the structure of the CPDS instruments, the detector assembly only allows detection of particles in a specific direction of the station's orientation. Thus, the CPDS instruments can only provide unidirectional angle coverage in detecting particles.

The CRaTER detector includes three pairs of 0.14 mm and 1 mm thick compensated silicon detectors 35 mm in diameter to measure high and low linear energy transfer (LET) through different depths of tissue equivalent plastic (TEP). The instrument measures primary and secondary radiation fluxes at various depth of shielding to validate LET models of space radiation. The geometry of the CRaTER was designed for simultaneous measurement of radiation coming from directly above and below through the different depths of the TEP. The geometry of the CRaTER instrument prevents the use of a Cherenkov detector, as the inclusion of material that is not the required TEP would negatively impact the usefulness of the CRaTER instrument for this simultaneous measurement.

While most space radiation particle detection instruments are the size of CPDS and CRaTER, some detection instruments are much larger. The Alpha Magnetic Spectrometer (AMS) is a large 7 metric ton particle detector. The detector includes eight silicon tracker layers inside a 0.8 T-m$^2$ magnet, having an acceptance area of 0.5 square meters. The detector further includes an electromagnetic calorimeter, time-of-flight scintillator system, and a Ring Imaging Cherenkov detector. The large size and complexity of this instrument directly conflicts with a need for miniaturized space radiation detectors and the reduction in mass and power needs of the space radiation detectors. Thus, the AMS is not suitable for this purpose.

Thus, a particle detector, in accordance with an embodiment of the present invention, which provides information on the kinetic energies, directions, and electric charges of highly energetic incident subatomic particles is described. The particle detector may allow improved solid angle coverage to incoming particles, may allow a smaller volume for a charged particle detector, and may allow for better energy resolution. Some embodiments of this particle detector, among other things, may increase solid angle coverage, compared to previous detectors, such as the CPDS and the CRaTER as shown in FIG. 1.

In particular, FIG. 1 highlights an increased solid angle coverage of an embodiment of the invention. At a minimum, the particle detector, in accordance with an embodiment of the invention, can result in an increased geometric factor (a measurement of detector aperture and solid angle coverage) of at least 1.1 cm$^2$sr, which would be larger than the geometric factor of the CPDS and CRaTER detectors, as shown in FIG. 1. However, one of ordinary skill in the art would readily understand that alternative embodiments may have increased geometric factor, as will be discussed below in more detail.

FIG. 2 is a diagram of the particle detector, in accordance with an embodiment of the invention.

The depicted particle detector 200 includes a spherical Cherenkov detector 210. The particle detector 200 further includes photodetectors 220, mounted on the spherical Cherenkov detector 210, configured to detect ultraviolet (UV) light emitted by particles traversing the spherical Cherenkov detector 210 at a certain speed. The particle detector 200 further includes pairs of detector stacks 230, mounted on the spherical Cherenkov detector 210 configured to detect particles traversing the radiation detector 200.

According to embodiments of the invention, each detector stack 230 may be used in identifying incident particles, and would respond to particles incident within a solid-angle range that, in conjunction with the number of stacked detectors 230, would define the angular resolution of the particle detector

200. In other words, a pair of detector stacks 230 may be used to determine a path length, a path direction, and a velocity of an incident particle. The detector stacks 230 may also serve as triggers for collection of UV light by photodetectors of the spherical Cherenkov detector 210, where the UV light is emitted from the incident particle. The UV light may enable the particle detector 200 to determine a charge, energy, and velocity of the particle. Thus, the particle detector 200 can determine a path length, path direction, charge, energy, and velocity of the particle.

In the depicted embodiment, the overall diameter of the particle detector 200 is no more than 18 cm. However, one of ordinary skill in the art would readily understand that the diameter of the particle detector 200 could exceed 18 cm in alternative embodiments, and be consistent with the concept of the invention.

The spherical Cherenkov detector 210 will now be described in more detail.

According to the exemplary embodiment of the invention, the spherical Cherenkov detector 210 includes a sphere of UV transparent material. The UV transparent material may have an index of refraction greater than 1 in UV. Examples of UV transparent material which may have an index of refraction greater than 1 include sapphire, quartz, and acrylic. The sphere is also coated by a UV reflecting material which includes open ports.

The spherical Cherenkov detector also includes photodetectors 220, which may be mounted to the sphere facing into the ports, according to the exemplary embodiment of the invention. The photodetectors 220 enable detection of Cherenkov UV light emitted by incident particles traversing within the sphere at a certain speed, and thus, interacting with the photodetectors 220. The photodetectors 220 may include semiconductor photodiodes based on silicon carbide or gallium nitride, or may use optical fiber from the ports to the photodiodes. As an alternative embodiment of the invention, the photodetectors 220 may use optical fiber from the ports to photomultiplier tubes.

The coating of the sphere with a UV reflective material, combined with the photodetectors 220 facing the ports, allows the sphere to become an integrating sphere increasing the charge and velocity sensitivity of the spherical Cherenkov detector 210. As one of ordinary skill in the art would readily understand, the theory of the integrating sphere is the theory of using multiple reflections in a cavity to measure total spectral reflectance.

Cherenkov detectors utilized in previous particle detectors do not take the form of a spherical structure. For example, the Cherenkov detector of the CPDS is the shape of a flat disk of sapphire of UV acrylic on a photomultiplier tube. The spherical Cherenkov detector 210, according to the exemplary embodiment of the invention, increases the directional sensitivity to many different directions, as compared to prior art particle detectors. Thus, unlike prior art detectors, which must be manually moved to be facing a different detection, the radiation detector 220 may detect particles in many different directions.

The pairs of detector stacks 230 will now be discussed in more detail. As previously discussed, the pairs of detector stacks 230 serve as triggers for collection of light by each photodetector 220 of the Cherenkov detector. Specifically, a detector stack 230 may detect an incident particle when the incident particle travels near the sphere. As the incident particle traverses the sphere, other detector stacks of the pairs of detector stacks 230 may also detect the particle. Based on the detector stacks that are triggered, a path length, a path direction, and a velocity of the particle may be determined. Thus, the presence of many detectors stacks at different angles may improve angular resolution as well as angular coverage.

One of ordinary skill in the art would readily understand that the depicted particle detector 200 is capable of having any number of detector stacks 230 and that each detector stack 230 is capable of having any number of detectors. Accordingly, one of ordinary skill in the art would readily understand that the particle detector 200 as depicted in FIG. 2 is an example embodiment of a particle detector according to the present invention, and does not limit the scope of the present invention to a particular number of detector stacks or number of detectors within each detector stack.

In certain embodiments, each detector stack 230 may comprise an area greater than 1 $cm^2$ detectors. However, one of ordinary skill in the art would readily understand that in other embodiments, the size of each detector stack 230 may be less than 1 $cm^2$.

Furthermore, the detectors in each detector stack 230 may be arranged in different configurations. In certain embodiments according to the invention, the detectors in each detector stack 230 may be of different thicknesses in order to accomplish sorting for lower velocity particles. However, one of ordinary skill in the art would readily understand that in other embodiments, the detectors in each detector stack 230 may be of the same thickness. In addition, in certain embodiments of the invention, sheets of energy moderating material may be inserted between detectors to allow discrimination of particles by energy. The energy moderating material may include, for example, tungsten, lead, nickel, iron, or their alloys. However, one of ordinary skill in the art would readily understand that in other embodiments, each detector stack 230 may not include any energy moderating material.

Thus, according to embodiments of the invention, each detector stack 230 may produce an increased solid angle coverage as compared to prior art detectors. Furthermore, according to embodiments of the invention, the detector stacks 230, altogether, may produce an increased spherical coverage as compared to prior art detectors.

In alternative embodiments of the invention, the particle detector 200 may use one or more scintillation counters as a particle trigger to detect particles traveling near the sphere in addition to the detector stacks 230. Furthermore, in other alternative embodiments of the invention, one or more scintillation counters may be used instead of the detector stacks 230.

The detectors within the detector stacks 230 will now be discussed in more detail. As discussed above, each detector within the detector stacks 230 may serve as a trigger for collection of light by the photodetectors 220 of the Cherenkov detector 210 by detecting an incident particle when the incident particle travels through the sphere.

In certain embodiments, according to the invention, each detector within the detector stacks 230 is a semiconductor diode detector, such as a silicon solid state detector. Semiconductors, such as silicon, are considered applicable for radiation detectors due to their ionization energy, high electron mobility, high density, and structural rigidity. Furthermore, the higher density of solid state detectors allow higher sensitivity to radiation with less mass and volume that would be required for other types of detectors. For example, the density of the media interacting with the radiation can be as high as 1000 times of that for other detectors. However, in other embodiments, the detector may be a scintillating detector or a gaseous ionization detector.

In certain embodiments of the invention, each detector within the detector stacks 230 is a wide-band semiconductor diode detector (i.e. low-noise detector) which reduces the noise floor associated with the signal produced by the low-noise detector. Noise floor refers to the fact that there is inherent noise in a signal produced by a detector. Energy resolution is limited primarily by the noise floor of the detectors. A low-noise detector improves energy resolution due to the fact that the low-noise detector comprises material which is less susceptible to this inherent noise. In certain embodiments of the invention, the low-noise detector is a silicon carbide (SiC) detector. SiC is considered to be a very radiation tolerant material due to its wider band gap and large displacement energy. Furthermore, a SiC detector has a demonstrated improved energy resolution over silicon detectors, and improvement in detector noise floor has been demonstrated in the use of SiC-based devices. However, in other embodiments, the low-noise detector may comprise an alternative material than SiC, such as gallium nitride, or diamond, which is less susceptible to signal noise, and thus improve energy resolution, in a similar fashion.

The particle detector 200 may determine the path length, path direction, charge, energy, and velocity of a particle based on the detected signal from the detectors of the detector stacks 230 and the emitted UV light from the photodetectors 220 of the Cherenkov detector 210.

With sufficient high velocity particles, as is typically found in space radiation, the signal strength from each photodetector 220 is proportional to the square of the particle charge times the path length defined by the triggered pair of detector stacks. Thus, in certain embodiments, a velocity distribution for sorted high energy ions may be determined for a variety of directions.

By correlating the detected signal from the Cherenkov detector 210, with the signal differences between the stacked detectors of different thickness, either with or without moderating material in-between, further sorting may be accomplished for lower velocity particles. As an alternative embodiment of the invention, the individual signals from the photodetectors 220 may be compared to further increase the precision of velocity and direction determination.

According to certain embodiments of the invention, the inclusion of several detectors of varied thickness may allow particle identification. Thus, according to the embodiment of the invention, the integration of detectors with moderators and absorbers may allow for estimation of electron, neutron, and ion flux. Furthermore, a combination of absorbers and converters in a detector stack may allow an understanding of particle energy and type.

In alternative embodiments of the invention, the spherical Cherenkov detector 210 may be replaced by a particle detector of similar or equivalent structure and function, but does not necessarily rely on the principles of a Cherenkov detector (i.e. detecting Cherenkov radiation).

FIG. 3 is a diagram of a detector stack in greater detail according to another embodiment of the invention. The detector stack 300 includes thick detectors 310, thin detectors 320, and energy moderating material, or in other words, moderator 330, electron converter 340, neutron converter 350, and absorber 360. In the depicted embodiment of the invention, slow ion 305, fast ion 315, electron 325, and neutron 335 (representing slow ions, fast ions, electrons, and neutrons, respectively) enter the detector stack. As the slow ion 305, the fast ion 315, and the electron 325, each pass through the thick detectors 310 and thin detectors 320, secondary electrons are generated that can be detected. Furthermore, if electron 325 is a fast-moving electron, electron 325 and neutron 335 also generate secondary electrons and positive ions as they pass the electron converter 340, and the neutron converter 350, respectively.

With respect to the moderator 330, as neutron 335 passes through the moderator 330, the neutron 335 slows down so that it will eventually be captured by the neutron converter 350. The absorber 360 shields thick detector 330 from stray secondary electrons and positive ions generated in electron converter 340, and neutron converter 350, respectively, to prevent misidentification of particles.

With respect to moderator 330, any material which slows down neutrons may be used. Furthermore, with respect to electron converter 340, any material with low ionization energy may used as a converter to detect fast electrons. However, according to an embodiment of the invention, aluminum is an ideal material due to its relatively low ionization energy and high radiation length.

With respect to neutron converter 350, any solid material (such as boron, uranium, neptunium, plutonium, or lithium), or any gaseous material (such as boron trifluoride or helium-3), that has a high capture cross section for neutrons may be used. However, according to an embodiment of the invention, boron carbide ($B_4C$) is an ideal material. With respect to absorber 360, any material which may be used to shield detectors from secondary electrons, such as nickel or lead, may be used.

The inclusion of a detector stack, surrounding a spherical Cherenkov detector, can improve system performance. According to certain embodiments of the invention, the stack detector may be less than 52 mm long, and may be designed to allow integration with the spherical Cherenkov detector.

As discussed above, the detector stack may have an unlimited number of detectors, the detectors may or may not be of the same thickness, and the detector stack may or may not have energy-moderating material inserted between the detectors. Thus, one of ordinary skill in the art would readily understand that the exact configuration of the detector stack according to the invention is not limited to the embodiment illustrated in FIG. 3. Furthermore, one of ordinary skill in the art would readily understand that one could modify the arrangement of the detector stack, with respect to the thickness of the detectors, and the presence of energy-moderating material, to focus on the detection of certain particles types, and filter out the other particle types.

According to another embodiment of the invention, as illustrated in FIG. 4, a geometry is defined to determine the minimum diameter of the sphere of the Cherenkov detector in the particle detector. According to the embodiment of the invention, the minimum size of the sphere is related to the square of the charge of a particle within the sphere and the width of the detector of the detector stack.

Cherenkov light emission energy per unit of path length (dE/dx) from a particle of charge ze with a fractional velocity $\beta$ of the speed of light traveling through a medium with an index of refraction $n(\omega)$, given as:

$$\left(\frac{dE}{dx}\right) = \frac{(ze)^2}{c^2} \int_{n(\omega)>1/\beta} \omega\left(1 - \frac{1}{\beta^2 n(\omega)^2}\right) d\omega$$

The integral is over all frequencies $\omega$ for $n(\omega)>1/\beta$, and c is the speed of light.

For sufficient high velocities ($\beta \rightarrow 1$), the light emission is dependent predominately on the charge and path length. For ions, the charge ze is the atomic number times the electronic charge. Thus, for an ion with an atomic number z traversing through the center of a sphere with a diameter D and radius r, the light intensity is proportional to the product $z^2 \cdot 2r$.

However, the ion is detected by both of a pair of directional detector stacks of a finite width w to define the path length through the sphere. The shortest path length through the sphere still detectable by the directional detector stack pair is shown in FIG. 4 as length L. The actual path length of a detected ion is thus between L and 2r based on the detector width w.

To be able to distinguish the light from an ion with an atomic number z and an ion with an atomic number of z+1, the light from the smaller ion over the longest path and the light from the larger ion over the shortest path must be distinguishable. That is, the sphere radius must be chosen such that the product $z^2 \cdot 2r$ must be smaller than the product $(z+1)^2 \cdot L$, or $z^2 \cdot 2r < (z+1)^2 \cdot L$.

Using the geometry from FIG. 4, the angle of the two ion paths $\theta$ is related to the width of the directional detector stacks such that $\sin \theta = w/2r$, and the path lengths are related such that $\cos \theta = L/2r$.

According to an embodiment of the invention, an estimate of the minimum diameter of the spherical Cherenkov detector may be less than five times the directional detector stack widths for all naturally occurring ions, thus allowing a compact detector size.

FIG. 5 is a flow diagram of a method for detecting a particle, in accordance with another embodiment of the invention. At step 500, a spherical Cherenkov detector is provided. The Cherenkov detector includes a sphere of ultraviolet transparent material. The sphere is coated by an ultraviolet reflecting material. The ultraviolet reflecting material includes an open port. The Cherenkov detector further includes a photodetector. The photodetector is mounted to the sphere and facing into the open port.

At step 505, a pair of detector stacks is provided. The pair of detector stacks is mounted to the Cherenkov detector. Each detector stack includes a detector configured to detect a particle traversing the sphere.

At step 510, ultraviolet light emitted from a particle within the sphere is detected, at the photodetector. At step 515, the particle traversing the sphere is detected, at each detector of the pair of detector stacks. At step 520, the path length, path direction, charge, energy, and velocity of the particle are each determined based on the detectors which detect the particle and the photodetector.

Figure 6:
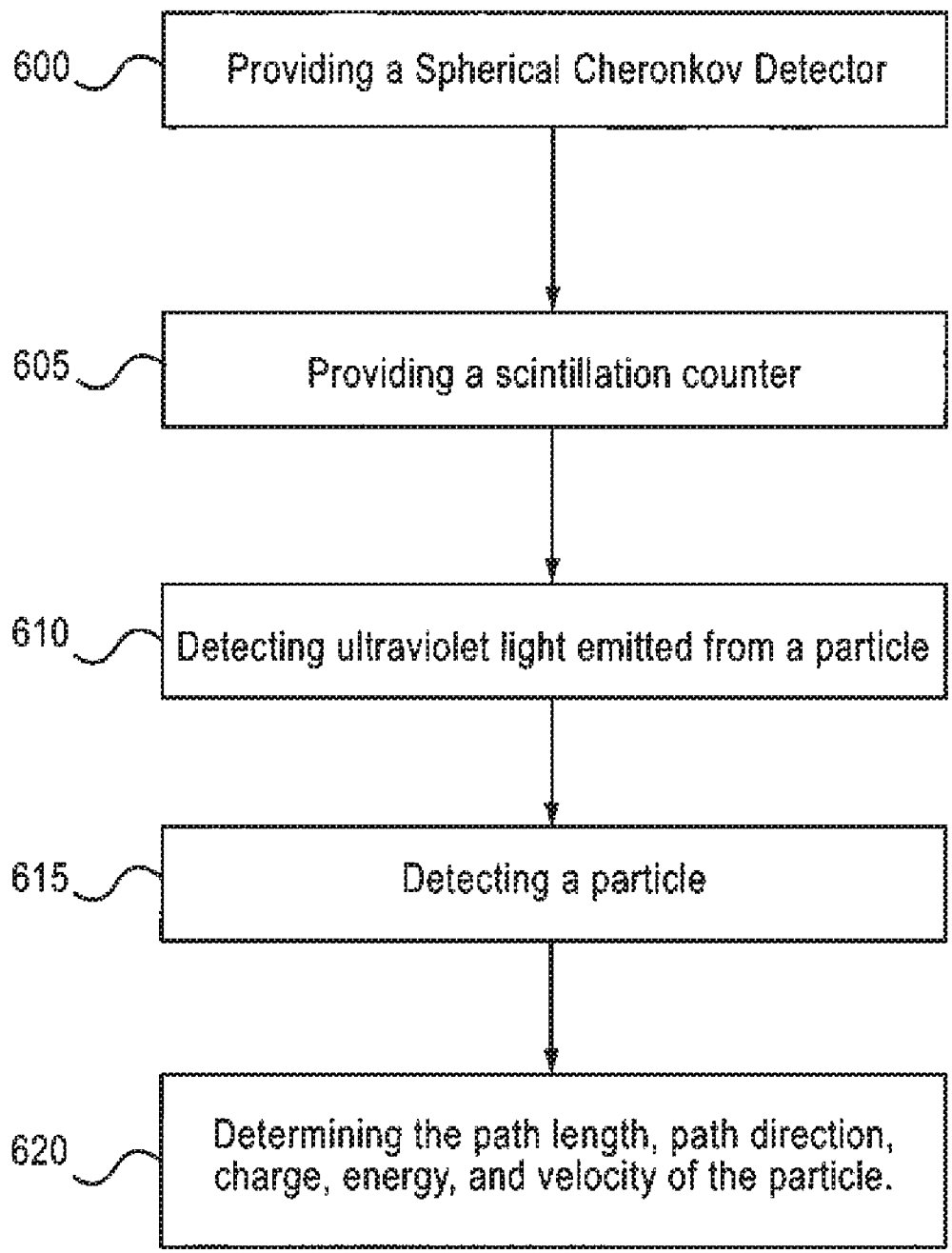
FIG. 6 illustrates a method of detecting a particle, according to another embodiment of the present invention.

FIG. 6 is a flow diagram of a method for detecting a particle, in accordance with another embodiment of the invention. At step 600, a spherical Cherenkov detector is provided. The Cherenkov detector includes a sphere of ultraviolet transparent material. The sphere is coated by an ultraviolet reflecting material. The ultraviolet reflecting material includes an open port. The Cherenkov detector further includes a photodetector. The photodetector is mounted to the sphere and facing into the open port.

At step 605, a scintillation counter is provided. The scintillation counter is configured to detect a particle traversing the sphere.

At step 610, ultraviolet light emitted from a particle within the sphere is detected, at the photodetector. At step 615, the particle traversing the sphere is detected, at the scintillation counter. At step 620, the path length, path direction, charge, energy, and velocity of the particle are each determined based on the scintillation counter and the photodetector.

Thus, embodiments of the invention may improve performance for future flight instruments. The spherical Cherenkov detector of the embodiments of the invention may allow improved solid angle coverage to incoming particles. The detector stack of the embodiments of the invention may allow for a smaller volume for a charged particle detector. The low-noise silicon carbide detectors of certain embodiments of the invention may allow for better energy resolution. Finally, integration of all of these technologies, according to embodiments of the invention, may result in an improved particle detector, in comparison to existing prior art particle detectors.

Certain embodiments of the invention may be used to measure properties of cosmic rays, such as radiation, in outer space. Alternative embodiments of the invention have applications beyond space science missions. For example, for planned manned lunar operations, there is a specific need for a solid state particle detector and an electron ionization detector on the outside of the spacecraft or rover. Embodiments of this invention may satisfy this need. Furthermore, alternative embodiments of the invention can be imbedded into a very high altitude aircraft. This can be very helpful to pilots and crew of high altitude flights, as radiation exposure is a significant concern. Finally, proton radiation therapy is becoming a more attractive option for treatment of both benign and cancerous tumors. Certain embodiments of this invention may be implemented for in vivo dosimetry, which may be useful in monitoring a patient's dose during treatment.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

We claim:

1. A radiation detector comprising:
   a sphere of ultraviolet transparent material;
   an ultraviolet reflecting material coating said sphere and having at least one open port therein;
   a photodetector configured to face the at least one open port; and
   at least one pair of detectors, wherein each detector is configured to detect a particle traversing the radiation detector so that the at least one pair of detectors determines a path length and a path direction of the particle traversing the radiation detector.

2. The radiation detector of claim 1, wherein the ultraviolet transparent material has an index of refraction greater than 1 in ultraviolet.

3. The radiation detector of claim 2, wherein the ultraviolet transparent material is sapphire, quartz, or acrylic.

4. The radiation detector of claim 1, wherein the photodetector comprises a semiconductor photodiode.

5. The radiation detector of claim 1, wherein the radiation detector further comprises an optical fiber, the optical fiber connected from the open port to the photodetector.

6. The radiation detector of claim 5, wherein the photodetector comprises a semiconductor photodiode or a photomultiplier tube.

7. The radiation detector of claim 1, wherein the radiation detector is configured to sort low velocity particles by correlating a signal generated by the photodetector with signal differences generated by each detector of the at least one pair of detectors.

8. The radiation detector of claim 1, further comprising a plurality of photodectors, and wherein the radiation detector is configured to compare a signal generated by each photodetector to further increase a precision of velocity and direction determination of the particle.

9. The radiation detector of claim 1, wherein the radiation detector is configured to identify the particle as a high velocity particle when a signal strength from the photodetector is proportional to the square of the charge of the particle times the path length of the particle.

10. The radiation detector of claim 1, wherein the photodetector is configured to detect ultraviolet light emitted from the particle so that the photodetector determines a charge, an energy, and a velocity of the particle.

11. The radiation detector of claim 10, wherein the at least one pair of detectors comprises at least one pair of detector stacks.

12. The radiation detector of claim 11, wherein each detector of the plurality of detectors is of a different thickness.

13. The radiation detector of claim 12, wherein each detector stack comprises one or more sheets of energy-moderating material, each sheet inserted between the plurality of detectors, each sheet configured to allow discrimination of particles.

14. The radiation detector of claim 13, wherein the sheet comprises tungsten, lead, nickel, iron, or alloys thereof.

15. The radiation detector of claim 14, wherein each sheet is a moderator, electron converter, neutron converter, or absorber.

16. The radiation detector of claim 1, wherein each detector of the at least one pair of detector stacks comprises a gaseous ionization detector.

17. The radiation detector of claim 16, wherein each detector of the at least one pair of detector stacks comprises a semiconductor diode detector.

18. The radiation detector of claim 17, wherein the semiconductor diode detector is a wide-band-gap semiconductor diode detector, and wherein the wide-band-gap semiconductor diode detector is based on silicon carbide, gallium nitride, or diamond.

19. The radiation detector of claim 1, wherein the at least one pair of detectors comprises at least one pair of scintillation counters.

20. The radiation detector of claim 19, further comprising a scintillation counter configured to operate as a particle trigger.

* * * * *